United States Patent
Petersen et al.

(10) Patent No.: US 9,212,435 B2
(45) Date of Patent: Dec. 15, 2015

(54) PULP AND FIBRILLATED FIBER COMPOSITE

(75) Inventors: Brent A. Petersen, Seattle, WA (US); Andrew J. Dodd, Seattle, WA (US); Andre S. Hajnal, Anderson Island, WA (US); Noriko Suzuki, Seattle, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 11 days.

(21) Appl. No.: 13/538,890

(22) Filed: Jun. 29, 2012

(65) Prior Publication Data

US 2014/0004326 A1    Jan. 2, 2014

(51) Int. Cl.
| | | |
|---|---|---|
| *D04H 1/425* | (2012.01) | |
| *D04H 1/4266* | (2012.01) | |
| *D04H 1/732* | (2012.01) | |
| *D21H 27/00* | (2006.01) | |
| *D21H 11/04* | (2006.01) | |
| *D21H 11/10* | (2006.01) | |
| *D21H 11/18* | (2006.01) | |
| *A61F 13/53* | (2006.01) | |

(52) U.S. Cl.
CPC ............ *D04H 1/425* (2013.01); *D04H 1/4266* (2013.01); *D04H 1/732* (2013.01); *D21H 11/04* (2013.01); *D21H 11/10* (2013.01); *D21H 11/18* (2013.01); *D21H 27/002* (2013.01); *A61F 2013/530021* (2013.01); *A61F 2013/530036* (2013.01); *A61F 2013/530072* (2013.01); *Y10T 428/268* (2015.01)

(58) Field of Classification Search
CPC ... D04H 1/425; D04H 1/4266; Y10T 428/268
USPC .......................................... 428/212, 220, 357
See application file for complete search history.

(56) References Cited

U.S. PATENT DOCUMENTS

| | | | |
|---|---|---|---|
| 4,755,421 A * | 7/1988 | Manning et al. ............... | 442/338 |
| 5,318,844 A * | 6/1994 | Brandon ....................... | 428/357 |
| 5,725,827 A | 3/1998 | Rhodes | |
| 6,042,769 A | 3/2000 | Gannon | |
| 6,653,406 B1 | 11/2003 | Soerens | |
| 6,841,038 B2 | 1/2005 | Horenziak | |
| 8,187,422 B2 | 5/2012 | Sumnicht et al. | |
| 2002/0064654 A1* | 5/2002 | Luo et al. ....................... | 428/364 |
| 2003/0177909 A1 | 9/2003 | Koslow | |
| 2005/0142973 A1 | 6/2005 | Bletsos | |
| 2010/0288456 A1 | 11/2010 | Westland et al. | |
| 2012/0043038 A1 | 2/2012 | Dodd | |

OTHER PUBLICATIONS

Konishi et al. (JP 2009-140474 machine translation).*

* cited by examiner

*Primary Examiner* — Aaron Austin
*Assistant Examiner* — Lawrence Ferguson
(74) *Attorney, Agent, or Firm* — Timothy M. Whalen; Weyerhaeuser Law Dept

(57) ABSTRACT

A cellulose pulp sheet is provided that is formed from never-dried kraft pulp and fibrillated fibers, such as lyocell. The pulp sheet provides several beneficial features as a result of both the use of fibrillated fibers and never-dried kraft pulp, particularly when the pulp sheet is used to form air-laid absorbent materials that include superabsorbent polymers.

23 Claims, 2 Drawing Sheets

PULP AND FIBRILLATED FIBER COMPOSITE

BACKGROUND

The use of cellulose fibers in absorbent materials is well known. Particularly, cellulose fibers can be combined with super-absorbent polymers (SAP) in order to form an absorbent composition. For example, commercial products combining cellulose fibers and SAPs include adult incontinence products, baby diapers, training pants, and feminine hygiene products.

During disposable absorbent product manufacturing there is an issue of dust. During the fiberization process there is a loss of material and the associated hazards along with airborne particulates.

Once the disposable absorbent product is formed it is also important to be able to keep the SAP in place and not have it shift or fall out during manufacturing, transport or use. SAP loss and migration leads to an underperforming absorbent product.

Many disposable absorbent products suffer from poor strength when wet. Maintenance of the structure of the absorbent product when wet is essential to contain the liquid absorbed.

However, improved absorbent products are still required for the constantly-evolving demands of consumer applications for absorbent products.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a wet-laid cellulose pulp sheet is provided. In one aspect, the pulp sheet is formed from: never-dried kraft pulp; and fibrillatable fibers.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
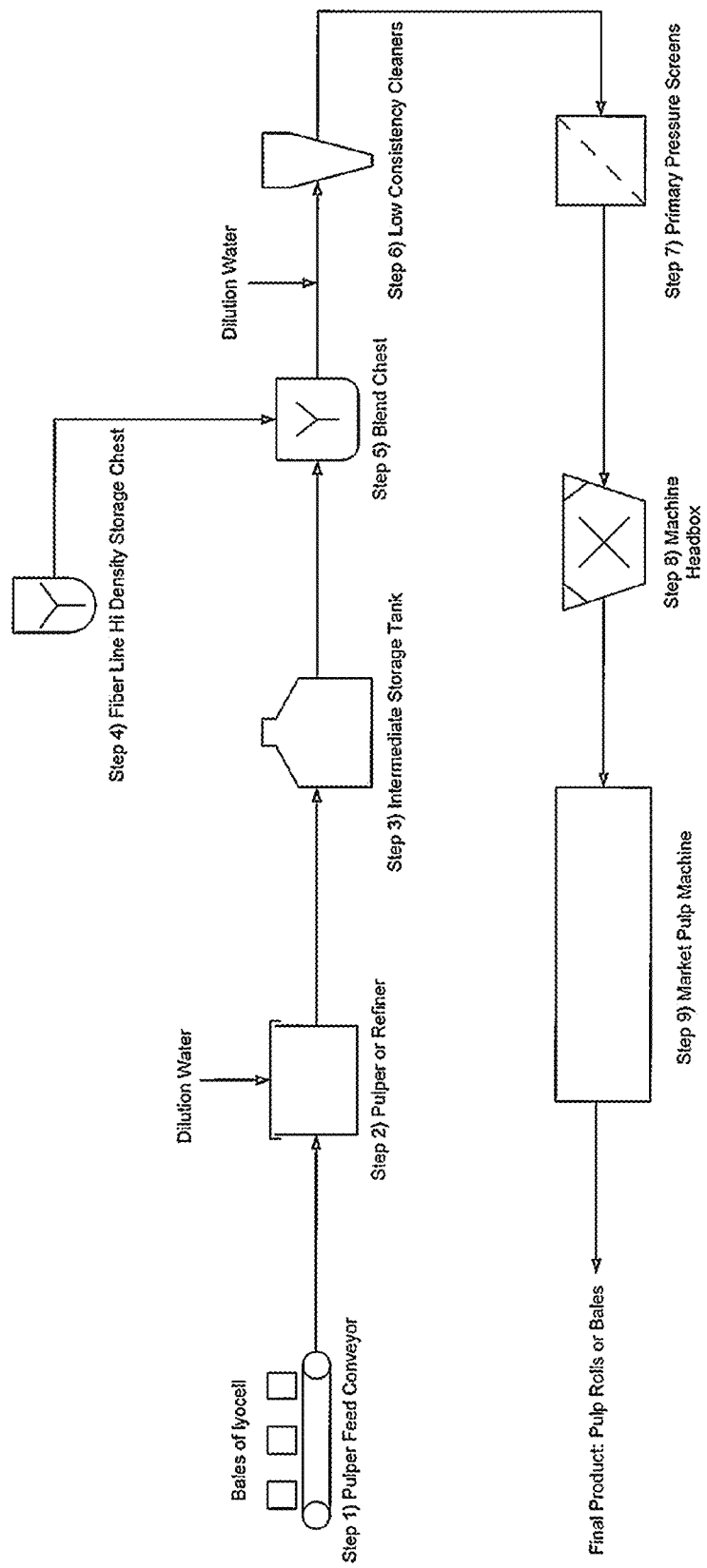
FIG. 1 illustrates a representative production process for a pulp sheet in accordance with the disclosed embodiments.

In one aspect, a cellulose pulp sheet is provided. In certain embodiments, the pulp sheet is formed from wood pulp and fibrillatable fibers. The wood pulp is preferably never-dried kraft pulp, which produces certain superior characteristics, as will be described in more detail below.

In certain embodiments, the pulp sheet is prepared by wet-laying a mixture of the fibrillated fibers and the wood pulp to form a porous sheet comprising between about 1 weight percent and 10 weight percent fibers and the balance in wood pulp, based on the total combined weight of wood pulp and fibers in the pulp sheet. Pulp sheets formed in this manner have the fibers and wood pulp substantially uniformly distributed throughout the pulp sheet.

In other embodiments, layers of pulp sheet and fibrillated fibers are laid in distinct layers to form the pulp sheet. For example, a multi-headbox fourdriner can be used to form such a pulp sheet. This would allow for two or more different fiber streams to be made in a layered product In certain embodiments, the pulp sheet consists essentially of never-dried kraft pulp and fibrillated fibers. As used herein, "consists essentially of" means that the composition includes at least the specified components, and may also include other components that do not materially affect the basic and novel characteristics of the invention. For example, no additional components are added to the pulp sheet during manufacture that improves the characteristics of the pulp sheet. Relatedly, in certain embodiments, the pulp sheet contains no binder or filler. For example, no fillers such as clay or others known to people skilled in the art are used. Additionally, no retention aides/wet strength additives such as kymene are used. Finally, no surfactants that are used as debonders are used to form the pulp sheet.

The pulp sheet can be characterized in a number of ways, as known to those of skill in the art. For example, in certain embodiments, the pulp sheet has a basis weight of from 300 to 900 g/m$^2$. In certain embodiments, the pulp sheet has a density of 0.4 to 1.5 g/cc.

In certain embodiments, the pulp sheet is from 0.5-4 mm thick. In certain embodiments, the pulp sheet has a fiberization energy of less than 160 kJ/kg. Fiberization energy requirement is determined using a laboratory scale hammermill instrumented to measure power necessary to fiberize a given weight of pulp. The mill used is a Kamas Laboratory Mill, Model H01, manufactured by Kamas Industri, AB, Vellinge, Sweden. The breaker bar clearance of the mill is set at 4.0 mm, the screen size is 19 mm, and rotor speed is adjusted to 3024 rpm. Samples are conditioned at 50% R.H. for a minimum of 4 hours prior to testing. The samples are cut into strips 5.0 cm wide and as long as the sample will permit. Sufficient strips are cut to yield about 150 g of fiberized pulp. Basis weight of the samples is known and the hammermill feed roller speed is adjusted to achieve a target feed rate of 2.80 g/sec In certain embodiments, the log reduction value (LRV) of the pulp sheet is less than 1. In certain embodiments, the log reduction value (LRV) of the pulp sheet is less than 0.8 LRV is determined using ASM F1608-00(2009).

The pulp sheet can be used to form any products known to those with skill in the art that are derived from pulp sheets. In this regard, the pulp sheet can be formed into a roll or bale for transportation to a suitable manufacturing facility.

One representative use for the pulp sheet disclosed herein is as a component of an absorbent material (e.g., an absorbent pad). It is known that superabsorbent polymers (SAP) can be incorporated into an absorbent pad, but the pulp sheet disclosed herein provides superior absorbent products when combined with SAPs. Particularly, if the pulp sheet is fiberized into substantially individual fibers and the fibers are formed into an air-laid sheet with SAPs, the air-laid sheet will have improved dry and wet integrity, as will be described in more detail below. In certain embodiments of the airlaid sheet, a superabsorbent polymer is present in the range of 25 to 80 wt % of the sheet. Any SAPs known to those of skill in the art can be used in the disclosed embodiments.

As a comparative example, U.S. Patent Application Publication No. 2005/0142973 (Bletsos et al), which is incorporated herein by reference in its entirety, discloses medical packaging formed using wood pulp and nanofibers. However, the composition of the materials disclosed by Bletsos et al. are distinct from those of the embodiments disclosed herein, particularly with regard to the nature of the pulp and fibers used, as well as the end products formed.

Cellulose Pulp

In certain embodiments, the cellulose pulp used to form the pulp sheet is never-dried pulp. "Cellulose pulp" or "wood pulp" as used herein refer to the product of boiling wood chips with alkaline liquors or solutions of acidic or neutral salts followed by bleaching with chlorine compounds, the object being to remove more or less completely the hemicelluloses and lignin incrustants of the wood. The pulping raw materials are sources of cellulose, hemicellulose and lignin and the terms "wood" or "tree" will be used to generically describe any source of cellulose, hemicellulose and lignin. In the wood pulping industry, trees are conventionally classified as either hardwood or softwood. Embodiments of the present disclosure utilize softwood as the source of wood for the pulp.

Examples of softwood species from which pulp is formed include, but are not limited to: fir such as Douglas fir and Balsam fir, pine such as Eastern white pine and Loblolly pine, spruce such as White spruce, larch such as Eastern or Siberian larch, cedar, and hemlock such as Eastern and Western hemlock.

The cellulose pulp is not fibrillated prior to incorporation into the pulp sheet.

In traditional manufacturing methods, cellulose pulp is dried and formed into rolls as a convenient packaging scheme for distribution. Dried pulp rolls are then transported from the pulp manufacturer to the end user who converts the dried pulp rolls into cellulose products (e.g., disposable absorbent products, etc.).

Never-dried pulp is not used to manufacture absorbent products for practical reasons. Primarily, in order to use never-dried pulp, the manufacturing facility for the absorbent product must be co-located with the manufacturing facility for the pulp itself. This is because pulp must be dried in order to transport. This co-location issue has not traditionally been seen as an impediment in the industry, however, because there are no known benefits to the use of never-dried pulp compared to dried pulp for absorbent products.

In the embodiments disclosed herein, however, the inventors have determined that never-dried pulp unexpectedly produces improvements over dried pulp when incorporated into the disclosed pulp sheets.

Specifically, absorbent products formed from pulp sheets formed from never-dried pulp perform better under the rotap test and the hang test. These tests will be described in more detail in the Examples below.

In certain embodiments, the pulp used to form the pulp sheet is kraft pulp. By using kraft pulp, the disclosed embodiments are improved compared to other pulping processes in the following ways.

The kraft pulping process is well known to those of skill in the art and will not be discussed in detail herein.

In certain embodiments, the pulp is a southern bleached softwood kraft (SBSK) pulp. SBSK pulp is typically produced from pine trees grown in the southeastern United States. SBSK is pulped using the kraft process and bleached. The disclosed embodiments are improved by using SBSK compared to other pulp types in the following ways.

First, SBSK has relatively long fiber length compared to hardwoods (HW). For example, comparing SBSK and HW produced by various Weyerhaeuser mills, it was determined that SBSK has a typical fiber length of about 2.5 mm, whereas HW has a typical fiber length of about 0.9 mm. The longer fiber length of SBSK results in improved structural stability and wicking rate of absorbent products formed using SBSK compared to HW. Accordingly, in one embodiment, the pulp has fibers with an average length of from 2-3 mm.

Similarly, the coarseness of SBSK was determined to be about 21 mg/100 m, whereas HW was about 10 mg/100 m. The higher coarseness of SBSK results in a decrease in specific surface area so a more uniform wicking rate is achieved. Increased coarseness also makes it easier to defiberize the pulp sheet. In certain embodiments, the pulp fibers have a coarseness of from 12 to 30 mg/100 m.

Fibrillated Fiber

In certain embodiments, the pulp sheet is formed with fibrillated fiber. The entire amount of fiber used to form the pulp sheet can be fibrillated or a mixture of fibrillated and un-fibrillated fiber can be used.

Examples of fibers that can be fibrillated include lyocell fibers, cellulose derivatives, cotton, kapok, select grades of rayon, acrylic, nylon, or other natural or synthetic fibers of incomplete crystallinity. Fibrillation is the peeling back or splintering of the fiber ends to form tiny "hairs" on the surface of the fiber. If the fiber is likened to a banana, small fibrils or sections of the fiber splinter and pull away like a banana peel. Fibrillated fibers can be prepared by subjecting fibers, such as chopped fiber tow, to repetitive stresses while minimizing further reduction in fiber length. The preferred weight weighted mean length for fibrillated fibers is between 2 and 12 mm. The fibers can be fibrillated in water in a device such as a blender, or in a beater or refiner machines known in the art.

As the fibers undergo these stresses, the fibers form fibrils ("hairs") as a result of weaknesses between amorphous and crystalline regions. In certain embodiments, the fibrillated fibers have fibrils with a diameter of 0.004 µm to 6 µm. Accordingly, such fibers may be called nanofibers. The term "nanofiber" as used herein refers to fibers having a diameter or cross-section between about 10 nanometers (nm) and 1000 nm (1 micrometer).

The fibers are preferably fibrillated nanofibers, such as those described in Koslow, Patent Application Publication No. U.S. 2003/0177909, which is hereby incorporated herein by reference in its entirety.

As disclosed in the Examples below, fiber length affects certain qualities, such as the wet integrity of absorbent pads made using the pulp sheet.

In certain embodiments, the fibrillated fiber is selected from the group consisting of a natural fiber and a polymer fiber.

Natural fibers, such as those formed from cellulose, can also be used to form the pulp sheet. An exemplary natural fiber material is lyocell. The term "lyocell" as used herein refers to fibers that are formed by spinning of a solution that is obtained by dissolving wood pulp in an organic solvent, such as an amine oxide. Methods for manufacture of lyocell fibers are known in the art. Lyocell has cellulose, and in some instances hemicellulose and lignin as main constituents. The usual starting materials for lyocell include, but are not limited to, trees, grass and recycled paper. Preferred starting materials are dissolving wood pulp (SW, HW) with the right viscosity and purity and Kraft pulp with right viscosity and purity. Their blends can be used too.

Test Methods

In the non-limiting examples that follow, the following test methods were employed to determine various reported characteristics and properties. ASTM refers to the American Society of Testing Materials.

Rotap ("dry integrity") testing is used to measure the ability of a sample to retain SAP and fines. In the test, handsheets (500 gsm) were fiberized in a swinging hammers Kamas mill with a 3 mm gap rotating at 3500 rpm. The feed rate was 0.76 m/min, and the screen had 12 mm diameter holes A mass of 4.0 grams of fiberized sample pulp sheet and 6.0 grams of Hysorb 8600 superabsorbent were fed into a six inch airlaid pad former and airlaid onto an 8 inch square of tissue. Production of such pads is well known in the art.

Pads were cut into 10×10 cm squares and densified to 0.17 g/cc. This sample pad is placed on a 4 mesh Tyler screen with a 200 mesh Tyler screen and a pan underneath. The Rotap is run for five minutes at 278 oscillations and 150 taps per minute, as specified by ASTM standards. The material collected on the 200 mesh screen was collected and the SAP and fines loss was determined.

The "hang test" is used to determine the strength of a material when wet. The test involves fiberizing a handsheet (500 gsm) in a swinging hammers Kamas mill with a 3 mm gap rotating at 3500 rpm. The feed rate was 0.76 m/min, and the screen had 12 mm diameter holes A mass of 4.0 grams of fiberized sample pulp sheet and 6.0 grams of Hysorb 8600 superabsorbent were fed into a six inch airlaid pad former and airlaid onto an 8 inch square of tissue. Production of such pads is well known in the art.

The above pads were densified to 0.17 g/cc and soaked in 200 g of 0.9% saline for 2 min. The pad is then carefully picked up by hand and hung over a 1.43 cm round bar. If the pad stays together for 2 min hanging on the rod it passes the hang test. If all or part of the pad drops off it fails the hang test.

The pad integrity test was used for wet and dry integrity. The test involves fiberizing a handsheet (500 gsm) in a swinging hammers Kamas mill with a 3 mm gap rotating at 3500 rpm. The feed rate was 0.76 m/min, and the screen had 12 mm diameter holes For dry integrity a mass of 8.0 grams of fiberized sample pulp sheet and 8.0 grams of Hysorb 8600 superabsorbent were fed into a six inch airlaid pad former and airlaid onto an 8 inch square of tissue. Production of such pads is well known in the art.

Pads were cut into 10×10 cm squares and densified to 0.17 g/cc. The sample is inserted into tester on Plexiglas circle with 32 mm diameter hole and a positioning template with a 90° positioning guide. Burst with a 16 mm diameter rod four times per pad, one in each corner.

For wet integrity a mass of 4.0 grams of fiberized sample pulp sheet and 6.0 grams of Hysorb 8600 superabsorbent were fed into a six inch airlaid pad former and airlaid onto an 8 inch square of tissue. Production of such pads is well known in the art.

Pads were cut into 10×10 cm squares and densified to 0.17 g/cc. The sample is inserted into tester on Plexiglas circle with 32 mm diameter hole and a positioning template with a 90° positioning guide. Burst with 16 mm diameter rod four times per pad, one in each corner.

To measure fibrillation, an aqueous slurry or fibers were mounted in de-ionized water on a microscope slide and their digitized microscopic images were traced and measured using ImageJ image analysis software calibrated with a glass mounted microscope scale.

Using a scanning electron microscope (SEM), the specimens were sputter coated with 60:40 Au:Pd and imaged at 7.5 KV. The diameters of the fibers and the fibrils were measured directly from SEM photos using ImageJ.

Another way to measure fiber length is by FQA. In this method, the fibers are measured by a method that is based on TAPPI 271 om-02—Fiber Length of Pulp and Paper by Automated Optical Analyzer and the Optest Equipment Inc. FQA Manual.

The following Examples are intended to illustrate, not limit, the present disclosure.

EXAMPLES

Example 1

Manufacture of Representative Pulp Sheet

While the pulp sheet can be manufactured using any methods known to those of skill in the art, the following is a representative method. FIG. 1 illustrates the method and the following steps describe the method of FIG. 1.

Step 1) 100% lyocell is used as the starting raw material for the fibrillation process.

Step 2) Water is added to lyocell in a pulper or refiner to fibrillate the lyocell through a mechanical shearing process in a batch process. The residence time in the pulper or refiner determines the state of fibrillation for the lyocell.

Step 3) The fibrillated lyocell is stored in tank(s) until blended with normal pulp.

Step 4) Unfibrillated pulp is prepared as normal on the fiber line.

Step 5) The target blend of lyocell and pulp is added to the blend chest.

Step 6) The lyocell/pulp blend continues through the pulp line process flow as normal with the blended material processing through low consistency cleaners.

Step 7) The lyocell/pulp blend is processed through the primary pressure screens in preparation for processing onto the pulp line.

Step 8) The lyocell/pulp blend is added to the pulp line machine headbox for pulp production.

Step 9) The headbox feeds a market pulp machine, producing either rolls or bales of market pulp.

Example 2

Rotap Testing

Pulp sheets were fiberized comprised of SBSK pulp and fibrillated lyocell with 6 mm fiber length. During fiberization it was also noticed that there was distinctly less dust generated because of the fibrillated lyocell. Both dried and never-dried SBSK pulp was used. The pads included SAP at 60 wt %. Rotap testing was performed to determine the ability of the pads to retain the SAP and fines. The data is summarized in Table 1. Notably, it was determined that increasing the lyocell content improves the retention of SAP and fines. Additionally, never-dried SBSK pulp samples show improved SAP and fines retention when compared to dried SBSK pulp samples having the same lyocell content.

TABLE 1

Rotap Test for SAP Loss

| Lyocell wt % | Dried Pulp SAP and Fines % Loss | Never-Dried Pulp SAP and Fines % Loss |
|---|---|---|
| 0 | 66.0 | 60.2 |
| 3 | 29.3 | 23.3 |
| 5 | 22.0 | 20.9 |

Figure 2:
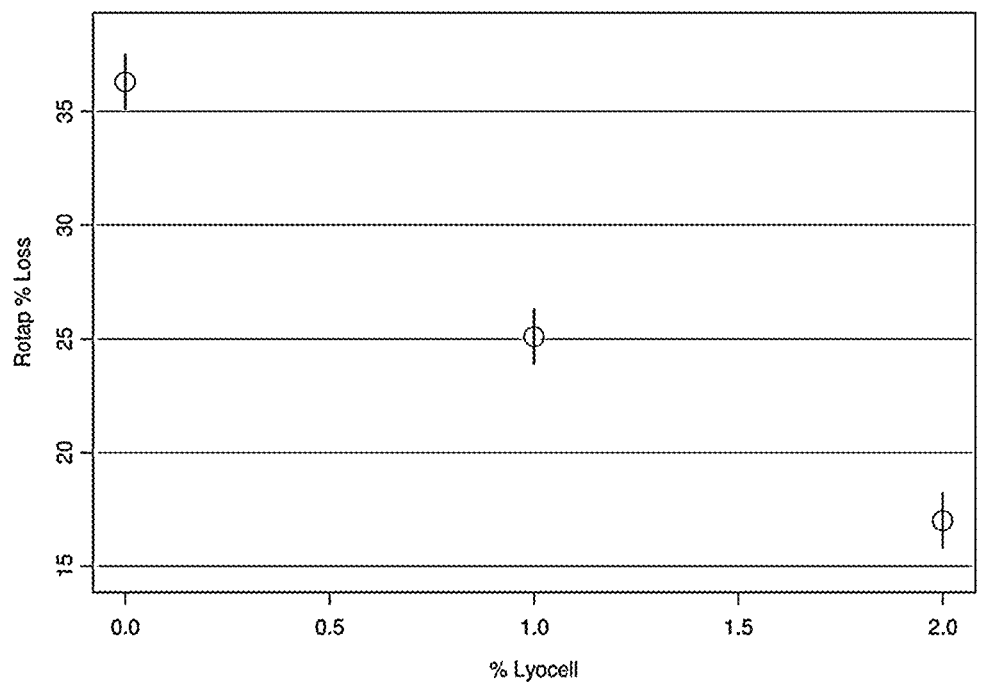
FIG. 2 graphically illustrates the relationship between rotap loss dry integrity and lyocell amount in an absorbent pad formed using a pulp sheet in accordance with the disclosed embodiments.

FIG. 2 additionally illustrates the impact a small addition of fibrillated lyocell can have on retention of SAP and fines during rotap testing. In FIG. 2, adding 1% lyocell reduces the SAP loss by over 10%. A further 1% addition of lyocell (2 wt % total) yields another drop of almost 10%. In these samples, the composition of the samples was once dried SBSK and 6 mm lyocell formed at 850 gsm with a density of 0.15 g/cc. The composition of the sample was 50% cellulose and 50% SAP.

Example 3

Wet Integrity

The wet integrity of SBSK/3 wt % 6 mm fibrillated lyocell was tested versus a control with no lyocell. 60% of SAP was added. The lyocell was fibrillated for 10 or 20 minutes. The samples were soaked for two minutes in 100 mL of 0.9% saline solution prior to testing. Testing was performed at 25 psi for 20 seconds. The average wet integrity was: control=10.16 N; 10 min fibrillation lyocell=13.32 N; and 20 min. fibrillation lyocell=12.10 N. Accordingly, adding fibrillated lyocell improves the wet integrity. Notably, the results imply that there is an optimum fibrillation degree for wet integrity. In the present example, the less-fibrillated sample had the highest wet integrity.

In a second, similar test, the wet integrity of SBSK/3 wt % fibrillated lyocell having lengths of 6 mm or 8 mm was tested versus a control with no lyocell. 60% of SAP was added. The average wet integrity was: control=4.5 N; 6 mm lyocell=6.1 N; and 8 mm lyocell=12.10 N. Accordingly, longer lyocell improves the wet integrity.

Example 4

Dry Integrity

Figure 3:
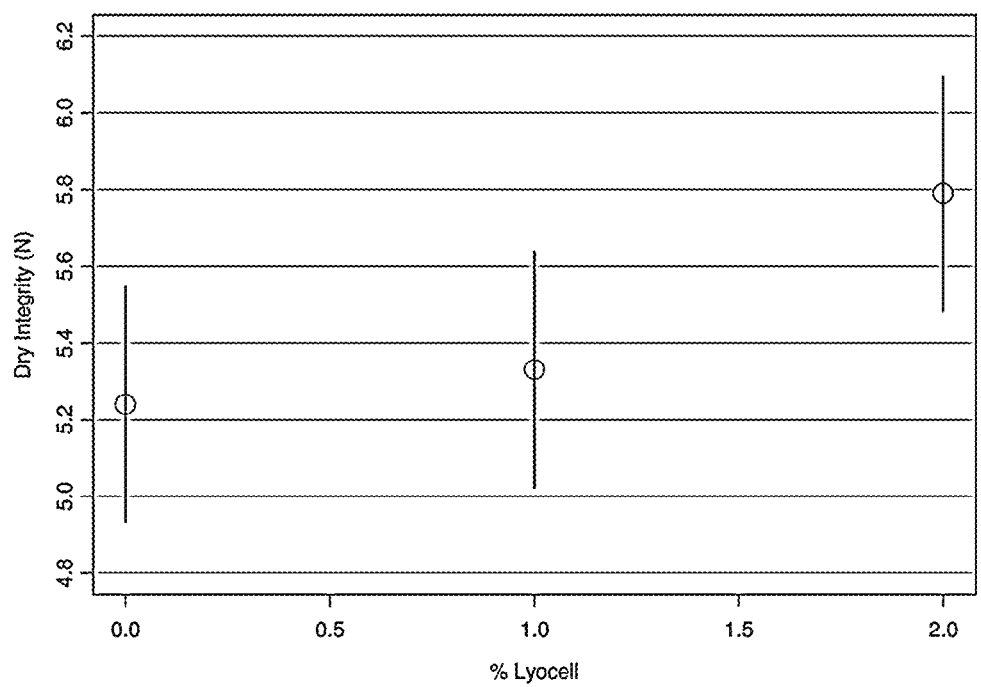
FIG. 3 graphically illustrates the relationship between dry integrity and lyocell amount in an absorbent pad formed using a pulp sheet in accordance with the disclosed embodiments.

FIG. 3 illustrates the impact a small addition of fibrillated lyocell can have on dry integrity. In FIG. 3, adding 2% lyocell produces a statistically significant improvement in dry integrity compared to a control sample with no lyocell and a sample with 1% lyocell. In these samples, the composition of the samples was once dried SBSK and 6 mm lyocell formed at 850 gsm with a density of 0.15 g/cc. The composition of the sample was 50% cellulose and 50% SAP.

Example 5

Hang Test

A comparative hang test was performed between a control and a sample absorbent pad in accordance with the embodiments disclosed herein. The control was 60% SAP and 40% SBSK pulp air-laid in a 6" diameter pad with a basis weight of 500 gsm soaked in 200 mL of saline. The sample was of similar composition but with lightly fibrillated (10 mins) lyocell 6 mm long added to the SBSK at 3 wt %. In the hang test the control dropped instantly, breaking along a seam formed on the testing bar, or could not be picked up and placed on the bar. The sample maintained integrity for the duration of the test, 2 minutes, without any sign of failure.

Further experimental results indicate that increasing the length (e.g., from 4 mm to 8 mm) of the lyocell fiber improves the hang test result, as does increasing the wt % (e.g., from 3% to 7%) of lyocell in the pulp sheet. Longer fibrillation improves the hang test result in some cases.

Additionally, the difference between dried and never-dried SBSK was tested using the hang test for samples such as those described above. It was determined that the never-dried samples were superior to the dried samples. Particularly, never-dried samples at 3 wt % lyocell with either 6 or 8 mm fiber length passed the hang test when similar dried samples failed the hang test.

Further, the hang test properties were able to be improved by having a long fibrillatable fiber present. Samples passed the hang test when the natural kapok fiber was added in at 3-7 wt % with the same trend for increasing the wt % that was seen with fibrillated lyocell.

While illustrative embodiments have been illustrated and described, it will be appreciated that various changes can be made therein without departing from the spirit and scope of the invention.

The embodiments of the invention in which an exclusive property or privilege is claimed are defined as follows:

1. A wet-laid cellulose pulp sheet formed from:
   unfibrillated, never-dried kraft pulp; and
   fibrillatable fibers;
   wherein the pulp sheet is from 1-10 weight % fibrillatable fibers; and
   wherein the kraft pulp has fibers with an average length of from 2-3 mm.

2. The pulp sheet of claim 1, wherein the kraft pulp is a southern bleached softwood kraft.

3. The pulp sheet of claim 1, wherein the kraft pulp has fibers with a coarseness of from 12 to 30 mg/100 m.

4. The pulp sheet of claim 1, wherein the fibrillatable fibers have an average length of from 2-25 mm.

5. The pulp sheet of claim 1, wherein the fibrillatable fiber is fibrillated.

6. The pulp sheet of claim 1, wherein the pulp sheet has a density of 0.4 to 1.5 g/cc.

7. The pulp sheet of claim 1, wherein the pulp sheet has a fiberization energy of less than 160 kJ/kg.

8. The pulp sheet of claim 1, wherein the pulp sheet is such that if it is fiberized into substantially individual fibers and the fibers are formed into an air-laid sheet with a superabsorbent polymer, when tested by the rotap method the air-laid sheet will retain 25% more SAP and fines than a pulp sheet that does not have fibrillatable fibers.

9. The pulp sheet of claim 1, wherein the pulp sheet is such that if it is fiberized into substantially individual fibers and the fibers are formed into an air-laid sheet with a superabsorbent polymer, the air-laid sheet will pass the hang test.

10. The pulp sheet of claim 1, wherein the fibrillatable fiber is selected from the group consisting of a natural fiber and a synthetic polymer fiber.

11. The pulp sheet of claim 1, wherein the fibrillatable fiber is lyocell.

12. The pulp sheet of claim 5, wherein the fibrillated fiber is lyocell.

13. A wet-laid cellulose pulp sheet formed from:
   unfibrillated, never-dried kraft pulp; and
   fibrillatable fibers;
   wherein the pulp sheet is from 1-10 weight % fibrillatable fibers, and has a density of 0.4 to 1.5 g/cc.

14. The pulp sheet of claim 13, wherein the kraft pulp is a southern bleached softwood kraft.

15. The pulp sheet of claim 13, wherein the kraft pulp has fibers with one or more of a fiber length from a coarseness of from 12 to 30 mg/100 m and an average length of from 2-3 mm.

16. The pulp sheet of claim 13, wherein the fibrillatable fibers have an average length of from 2-25 mm.

17. The pulp sheet of claim 13, wherein the fibrillatable fiber is fibrillated.

18. The pulp sheet of claim 13, wherein the pulp sheet has one or more of a density of 0.4 to 1.5 g/cc and a fiberization energy of less than 160 kJ/kg.

19. The pulp sheet of claim 13, wherein the pulp sheet is such that if it is fiberized into substantially individual fibers and the fibers are formed into an air-laid sheet with a super-absorbent polymer, when tested by the rotap method the air-laid sheet will retain 25% more SAP and fines than a pulp sheet that does not have fibrillatable fibers.

20. The pulp sheet of claim 13, wherein the pulp sheet is such that if it is fiberized into substantially individual fibers and the fibers are formed into an air-laid sheet with a super-absorbent polymer, the air-laid sheet will pass the hang test.

21. The pulp sheet of claim 13, wherein the fibrillatable fiber is selected from the group consisting of a natural fiber and a synthetic polymer fiber.

22. The pulp sheet of claim 13, wherein the fibrillatable fiber is lyocell.

23. A wet-laid cellulose pulp sheet formed from:
unfibrillated, never-dried kraft pulp; and
fibrillatable fibers;
wherein the pulp sheet is from 1-10 weight % fibrillatable fibers, and
wherein the pulp sheet contains no binder or filler.

\* \* \* \* \*